(12) United States Patent
Dragotta et al.

(10) Patent No.: US 6,737,263 B2
(45) Date of Patent: May 18, 2004

(54) POLYHYDROXYALKANOATE LEVELS AS AN INDICATOR OF BIOREACTOR HEALTH

(75) Inventors: Dominic A. Dragotta, Elkton, MD (US); Vasantha Nagarajan, Wilmington, DE (US); Stuart M. Thomas, Wilmington, DE (US)

(73) Assignee: E. I. du Pont de Nemours and Company, Wilmington, DE (US)

( * ) Notice: Subject to any disclaimer, the term of this patent is extended or adjusted under 35 U.S.C. 154(b) by 177 days.

(21) Appl. No.: 09/940,298

(22) Filed: Aug. 28, 2001

(65) Prior Publication Data

US 2002/0052016 A1 May 2, 2002

Related U.S. Application Data

(60) Provisional application No. 60/231,025, filed on Sep. 8, 2000.

(51) Int. Cl.[7] .............................................. B09B 3/00
(52) U.S. Cl. ..................................... 435/262; 435/286.5
(58) Field of Search ........................ 435/6, 262, 262.5, 435/286.5; 201/903; 210/610, 611, 614, 615, 631

(56) References Cited

U.S. PATENT DOCUMENTS 5,013,441 A * 5/1991 Goronszy .................... 210/605
5,466,604 A   11/1995 Maneshin et al.
5,968,801 A * 10/1999 Saito et al. .................. 435/197

FOREIGN PATENT DOCUMENTS

JP          03 236784       10/1991
WO       WO 0052189 A1      9/2000

OTHER PUBLICATIONS

Barak Y. Atypical Polyphosphate Accumulation by the Denitrifying Bacterium P. denitrificans. Applied and Environmental Microbiology Mar. 2000 66(3)1209–1212.*
Brdjanovic D. Bioassay for Glycogen Determination in Biological Phosphorus Removal Systems. Water Science Technology 1998 37(4–5)541–547.*
Chuang S. Evaluation of Phosphorus Removal in Anaerobic Anoxic Aerobic System via PHA Measurements. Water Science Technology 1998 38(1)107–114.*
Lee S. Production and Degradation of PHA in Waste Environment. Waste Management 1999 vol. 19, 133–139.*
You S. The Characteristic of Phosphorus Uptake/Release of a Nutrient Removal Process Under Anoxic Condition. J of the Chinese Institute of Environmental Engineering 10(3)249–254, 2000.*

Beun, J. J., V. Verhoef, V. L. M.C.M. and H. J.J. 2000. Stoichiometry and kinetics of PHB metabolism under denitrifying conditions in activated sludge cultures. Biotech and Bioeng vol. 68: pp. 496–507.
Bond, P.L. et al., 1999, Microbiological aspects of phosphorus removal in activated sludge systems. Microbiol. Act. Sludge 227–256: 354–409.
Byrom, D., 1994, Polyhydroxyalkanoates. Plastics from Microbes. D. Mobley. New York, Hanser Publishers: 5–33.
Constantin, H. and M. Fick 1997. Influence of C–Sources on the Denitrification rate of a High Nitrate c oncentrated Industrial Wastewater. Water Research 31: 583–589.
Dawes, E. A. and P. J. Senior 1973. The role and regulation of energy reserve polymers in micro–orgamisms. Adv. Microb. Physiol. 10: 135–266.
Satoh et al, 1999. PHA production by activated sludge. Int. J. Biol. Macromol. 25: 105–109.
Isaacs, S, T. Mah and S. K. Maneshin 1998. Automatic Monitoring of Denitrification Rates and Capacities in Activated Sludge Processes using Fluorescence or Redox Potential. Water Science and Technology 37: 121–129.
Lee, S. Y. and J.–I. Choi 1999. Production and degradation of polyhydroxyalkanoates in waste environment. Waste Management 19: 133–139.
Louie. T. M., T. J>Mah, W. Oldham and W. D. Ramey 2000. Use of metabolic inhibitors and gas chromotography/mass spectrometry to study poly–B–hydroxyalkanoates metabolism involving cryptic nutrients in enhanced biological phosphorous removal systems. Water Res. 34: 1507–1514.
Riis, X and X. Mai 1988. Gas Chromatographic Determination of Poly–B–hydroxybutyric acid in Microbial Biomass after Hydroxhloric acid Propanolysis. Journal of Chromatography 445: 285–288.
Steinbuechel, A., et al., 1992, Molecular basis for biosynthesis and accumulation of polyhydroxyalkanoic acids in bacteria. FEMS Microbiol. Rev. 103: 217–230.
Thomsen, J. K., T. Geest and R. P. Cox 1994. Mass spectometric studies of the effect pH on the accumulation of intermediates in denitrification of Paracoccus denitrificans. Applied Environmental Microbiology 60: 536–541.

* cited by examiner

*Primary Examiner*—Ralph Gitomer

(57) ABSTRACT

A method has been developed to monitor the health of an activated sludge environment in a wastewater process comprising monitoring the levels of polyhydroxyalkanoates (PHA) produced and correlating those levels with various selected sample parameters. In general, levels of PHA in excess of about 15% to about 20% dry weight of the biomass is an indication that the biocatalytic efficiency of the wastewater treatment process is impaired.

11 Claims, 7 Drawing Sheets

POLYHYDROXYALKANOATE LEVELS AS AN INDICATOR OF BIOREACTOR HEALTH

This application claims the benefit of U.S. Provisional Application No. 60/231,025 filed Sep. 8, 2000.

FIELD OF THE INVENTION

The present invention relates to methods for monitoring and controlling biological activity in wastewater and controlling the treatment thereof. Specifically a method has been developed that correlates the production of polyhydroxyalkanoates (PHA) with bioreactor health and biocatalytic efficiency.

BACKGROUND OF THE INVENTION

A number of devices and systems to process and purify water from industrial operations and municipal sources prior to discharging the water are known. Activated-sludge wastewater treatment plants, which are well known in the art, have been most often utilized to address this problem. Additionally, many industrial and municipal water treatment plants utilize biological systems to pre-treat their wastes prior to discharging into the usual municipal treatment plant. In these processes, the microorganisms used in the activated sludge break down or degrade contaminants for the desired water treatment. Efficient process performance and control requires quick and accurate assessment of information on the activity of microorganisms. This has proven to be a difficult task in view of the wide variety of materials and contaminants that typically enter into treatment systems. Variations in the quantity of wastewater being treated, such as daily, weekly or seasonal changes, can dramatically change numerous important factors in the treatment process, such as pH, temperature, nutrients and the like, the alteration of which can be highly detrimental to proper wastewater treatment. Improperly treated wastewater poses serious human health dangers. It is imperative therefore to maintain the health and biocatalytic efficiency of these activated sludge systems.

Various biological processes are currently used in wastewater treatment plants to assist in contamination degradation. In a typical process, contaminants in the wastewater, such as carbon sources (measured as biological oxygen demand or BOD), ammonia, nitrates, phosphates and the like are digested by the activated sludge in anaerobic, anoxic and aerobic stages, also known in the art. In the anaerobic stage, the wastewater, with or without passing through a preliminary settlement process, is mixed with return activated sludge.

The goal of wastewater bioreactors is to mineralize inlet organic and inorganic compounds (nitrogen oxides e.g., nitrate, nitrite, and ammonia) to carbon dioxide and nitrogen gas resulting in a clean effluent stream. The efficiency of industrial wastewater treatment systems is especially important since loss of performance/capacity to treat process wastewater translates to lower manufacturing up time. Presently, there are no rapid methods to assess the biocatalytic capacity of wastewater reactors.

Currently, crude macroscopic parameters are used to gauge the performance of wastewater bioreactors. These crude macroscopic parameters include: exit carbon as measured by COD (chemical oxygen demand) or TOC (Total Organic Carbon); exit nitrogen by Total Kjeldahl Nitrogen (TKN) and exit phosphate by Ion Chromotography. While measurements of effluent leakage of exogenously supplied carbon, such as methanol and organic acid, could be used to identify an impaired bioreactor, these compounds would not be reliable indicators of bioreactor health because many other processes can impact the amount of carbon removed. Furthermore, assessment of performance using these metrics results in a responsive operating strategy, i.e., changes to reactor loads that are made only after deviation from the desired performance is observed. Finally, the catalytic activity of the biomass present in the bioreactors is time consuming to measure. For example, the denitrification rate is determined by removing biomass from the reactor and performing a batch rate study; taking about 1–2 days to perform, and therefore cannot be used to gauge the current denitrification capacity of the reactor. These batch studies are useful in establishing long term performance characteristics. To date, there have been no reports describing the relationship between cell physiology and catalytic capacity wastewater bioreactors.

The above methods are useful for monitoring the health of activated sludge systems however they contain several drawbacks including the inability to accurately predict a reduction or loss of denitrification activity in the system before nitrate or one of the denitrification intermediates is present in the bioreactor. This results in nitrate leakage or incomplete denitrification that is highly detrimental and undesirable to such systems. An improved method of tracking biocatalytic efficiency is needed, particularly with respect to denitrification potential.

The problem to be solved, therefore is to provide a facile, highly responsive method of monitoring activated sludge environments to rapidly predict loss of denitrification activity and other indicators of biocatalytic efficiency such as the concentrations of nitrate, ammonia, sulfate, phosphate and carbon dioxide in the system.

SUMMARY OF THE INVENTION

The present invention provides reliable methods to monitor bioreactor health and to maintain viable cultures within the bioreactor. Specifically, Applicants have solved the above-stated problem by making the correlation between the production of an internal storage molecule and denitrification rate as a control strategy. This internal storage molecule may be a class of storage molecules, collectively termed polyhydroxyalkanoates (PHA), or glycogen or the like. Preferably, this internal storage molecule is polyhydroxyalkanoates (PHA). The PHA level in the bacteria of the activated sludge can be easily measured and controlled by the level of nutrients (ammonia, phosphate, sulfate) in the bioreactor.

Specifically, the present invention provides a method for monitoring and controlling the biocatalytic efficiency of a wastewater treatment process comprising: a) providing an activated sludge environment comprising:
  (i) a carbon influx;
  (ii) cultures of autotrophic, heterotrophic and facultative microorganisms;
  (iii) feed nutrients; and
  (iv) an end electron acceptor; b) sampling wastewater from anaerobic, anoxic and/or aerobic stages of the treatment process; c) measuring the concentration of polyhydroxyalkanoates present in the sample to determine the status of selected sample characteristics; and d) adjusting the feed nutrients in the activated sludge environment depending on the status of the selected sample as measured in c), whereby the biocatalytic efficiency of a wastewater treatment process is controlled.

An indication that the biocatalytic efficiency of the wastewater treatment process is impaired is seen when the polyhydroxyalkanoates concentration is greater than about 15 to about 20 dry weight percent of the biomass. Preferably, the feed nutrients are adjusted accordingly in the activated sludge environment when the PHA concentration is from about 10 to about 20 dry weight percent of the biomass. More preferably, the feed nutrients are adjusted accordingly in the activated sludge environment when the PHA concentration is from about 10 to about 15 dry weight percent of the biomass.

Sample characteristics are selected from the group consisting of efficiency of denitrification, nitrate concentration, ammonia concentration, sulfate concentration, phosphate concentration and carbon dioxide concentration. Similarly, feed nutrients are selected from the group consisting of nitrate, ammonia, sulfate, sulfide, urea and phosphate. In addition, an end electron acceptor is selected from the group consisting of oxygen, nitrate, nitrite, nitrous oxide, ferric oxide, and sulfate.

The invention additionally provides a method of maintaining viable cultures in an activated sludge environment in the absence of carbon influx comprising: a) providing an activated sludge environment comprising:
(i) a carbon influx;
(ii) cultures of autotrophic, heterotrophic and facultative microorganisms;
(iii) feed nutrients; and
(iv) an end electron acceptor; b) removing the feed nutrients from the activated sludge environment while continuously monitoring the concentration of polyhydroxyalkanoates present in the activated sludge environment; c) removing the carbon influx from the activated sludge environment when the concentration of polyhydroxyalkanoates is greater than about 15 to about 20 dry weight percent of the biomass; and d) adding a minimal concentration of nitrate to the activated sludge environment of step c); whereby the cultures of autotrophic, heterotrophic and facultative microorganisms are maintained in a viable state in the absence of a carbon influx.

In a preferred embodiment, the carbon influx is removed from the activated sludge environment when the concentration of PHA is about 20 dry weight percent of biomass or greater.

In another preferred embodiment, the minimal concentration of nitrate added to the activated sludge environment of step c) is based on the COD content of the PHA in the biomass. Specifically, the COD provided by the PHA is equal to the fraction of PHA times the total dry biomass times fraction of carbon in PHA times the conversion factor for TOC to COD and is represented by Equation 1.

PHA COD(mg/L)=(0.2 mg PHA/mg MLSS)×[MLSS(mg/L)]× (0.556 mg C/mg PHA)          EQUATION 1:

The amount of nitrate that can be added to the activated sludge environment is equal to the COD provided by the PHA multiplied by the amount of nitrate-N reduced/COD)× (4.5 mg nitrate/mg nitrate-N).

Figure 1:
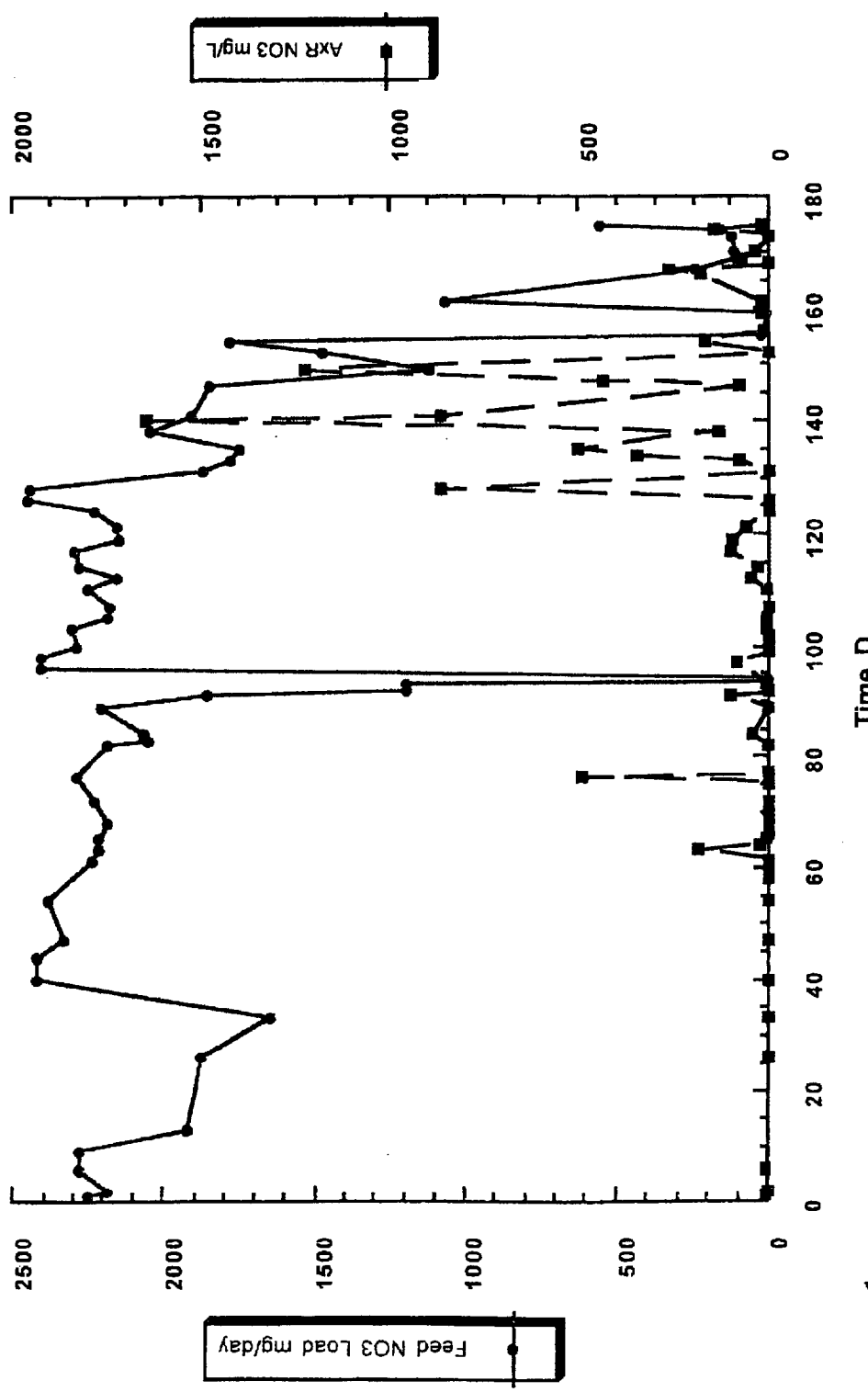
FIG. 1 shows a Macroscopic Reactor Performance without Ammonia. Nitrate load in mg/d (closed circle), Nitrate exiting reactor in mg/L (squares). Lines are drawn to indicate data trends. Arrow 1: Switch from methanol rich feed to organic acids rich feed. Arrow 2: First reactor shut down. Arrow 3: Second reactor shut down.

The invention can be more fully understood from the following detailed description.

DETAILED DESCRIPTION OF THE INVENTION

The present invention is useful for monitoring and controlling bioreactor health and bioreactor catalytic efficiency in an activated sludge environment by correlating the level of denitrification in the sludge with the production of an internal storage molecule. This internal storage molecule may be polyhydroxyalkanoates (PHA), glycogen, or the like. Preferably, this internal storage molecule is polyhydroxyalkanoates (PHA).

The method of the invention comprises providing an activated sludge environment that comprises a number of elements including a carbon influx, a variety of autotrophic, heterotrophic and facultative microorganisms, feed nutrients and at least one type of end electron acceptor to support respiration by the heterotrophic bacteria. Wastewater from the activated sludge system is then sampled from any of the anaerobic, anoxic, and/or aerobic stages of the bioreactor and the concentration of the internal storage molecule(s) is measured in the sample's bacteria according to methods well known in the art. A preferred method of measuring PHA levels is the method described by Riis and Mai, 1988 (*Journal of Chromatography*, 445:285–289) as outlined infra in the General Methods section of the Examples. Glycogen levels can be determined according to the methods described within Gerhardt et al. (*Manual of Methods for General Bacteriology*, American Society for Microbiology, Washington, D.C., 1981). Levels of PHA in excess of 15%–20% dry weight percent of the biomass indicate that the biocatalytic efficiency of the wastewater treatment process is impaired, and that denitrification potential in particular may be compromised. Feed nutrients may be adjusted accordingly to reverse the imbalance. Preferably, the feed nutrients are adjusted accordingly in the activated sludge environment when the PHA concentration is from about 10 to about 20 dry weight percent of the biomass. More preferably, the feed nutrients are adjusted accordingly in the activated sludge environment when the PHA concentration is from about 10 to about 15 dry weight percent of the biomass.

In this disclosure, a number of terms and abbreviations are used. The following definitions are provided.

The term "biocatalytic efficiency" will mean the specific removal rate of the target compound e.g., grams of organic removed per grams of biomass per time. Biocatalytic efficiency is generally considered impaired when the levels of PHA within the biomass are in excess of about 15 to about 20 dry weight percent of the biomass.

The term "denitrification" relates to a biological anaerobic process that occurs under reduced conditions in which nitrate acts as the electron acceptor to convert nitrate or nitrite to gaseous products. Many bacteria are able to perform this denitrification process to first reduce nitrate to nitrite, and then nitrite to nitric oxide (NO), nitrous oxide ($N_2O$), and finally nitrogen gas ($N_2$). Within a wastewater activated sludge environment, denitrification or nitrate reduction is a key process that is required to effectively treat wastewater prior to effluent release.

The term "denitrification efficiency" will mean the extent of reduction of nitrate or nitrite to the desired end product dinitrogen ($N_2$).

The term "denitrification potential" will mean the rate of reduction of nitrate to dinitrogen by a unit of biomass.

The term "wastewater treatment process" will mean a biological reactor system comprising an activated sludge environment that has the ability to degrade various organic compounds and other persistent pollutants. As used herein the term "activated sludge environment" will mean the mixture of wastewater, bacteria, and nutrients needed to maintain the health of the bacteria and effect the biocatalytic degradation of organic molecules.

The term "carbon influx" will mean the composition of organic material entering into a wastewater treatment process. The carbon influx will typically contain a variety of aromatic and straight chain organic molecules from industrial processing streams. With regard to the composition of organic material entering into a wastewater treatment process as carbon influx, this influx may comprise organic compounds selected from the group consisting of amines, alcohols, organic acids, carbohydrates, proteins, and amino acids.

The term "selected sample characteristics" refers to the characteristics of a wastewater sample that is tested for PHA concentrations. Selected sample characteristics typically define the health of a wastewater system and will relate to concentrations of various nutrients, including but not limited to nitrate, ammonia, sulfate, sulfide, urea, phosphate and carbon dioxide.

The term "feed nutrients" means various nutrients necessary to maintain the health and biocatalytic efficiency of the activated sludge environment. The components that comprise a wastewater system generally include an organic source (e.g., carbohydrates, organic acids and alcohols, amino acids, peptides, and/or aromatics), an end electron acceptor (such as oxygen, nitrate, nitrite, nitrous oxide, sulfate, and/or ferric iron), and "feed nutrients" (sulfate, sulfide, phosphate, and a nitrogen source, such as nitrate, ammonia, and/or urea). The organic source supplies energy and carbon molecules for anabolism. The end electron acceptor functions as the molecule that is reduced during energy generation. Feed nutrients are needed as building blocks for macromolecule synthesis of cellular constituents such as amino acids, deoxyribonucleotides, ribonucleotides, and phospholipids. Preferably, more than one nutrient is present in the feed nutrients. In a specific embodiment of the invention, the feed nutrients comprise free ammonia, a sulfate, and potassium phosphate or ammonium phosphate as nutrients.

The term "end electron acceptor" will mean a molecule that is reduced as a result of microbial respiration. Examples include, but are not limited to, oxygen, nitrate, nitrite, nitrous oxide, ferric oxide, and sulfate.

The term "nitrate-N" will mean the amount of nitrogen present per mole of nitrate. The conversion factor is 4.5 g nitrate/g nitrogen. Therefore, 20 mg/L nitrate-N is equal to 90 mg/L nitrate.

The term "mixed liquor suspended solids" or "MLSS" refers to the dry weight of the biomass in the system and is measured by drying to completion a known volume from the bioreactor at 105° C.

The term "mixed liquor volatile suspended solids" or "MLVSS" refers to the weight of volatile suspended solids in the system and is determined by heating the dried sample at 550° C. for 30 min, followed by cooling to room temperature in a dessicator, and measuring the weight. "MLVSS" is calculated by subtracting the residual weight of the sample following the 550° C. heating step from "MLSS" weight.

The terms "activated sludge bacteria", "activated sludge microorganisms" or "sludge" will refer to autotrophic, heterotrophic and facultative microorganisms that are typically found in wastewater systems and possess the enzymatic machinery to degrade compounds found in carbon influx.

Activated Sludge Environment

The present invention provides an activated sludge environment comprising a number of components including a carbon source, a variety of autotrophic, heterotrophic, and/or facultative bacteria, and feed nutrients required for the growth and biocatalytic health of the biomass. Preferably, all three types (autotrophic, heterotrophic and facultative) of bacteria are present.

The term "autotrophic bacterium" or "autotrophic bacteria" will mean an organism or organisms capable of growing on inorganic nutrients and using carbon dioxide as its sole carbon source.

The term "heterotrophic bacterium" or "heterotrophic bacteria" will mean an organism or organisms that requires one or more organic nutrients, including an organic carbon source for growth, e.g., the requirement of glucose by *Escherichia coli* for growth.

The term "facultative bacterium" or "facultative bacteria" will mean an organism or organisms that can switch easily from one growth physiology to another. For example, bacteria that can switch to nitrate as an electron acceptor in the absence of oxygen.

The types of bacteria that may be present in the activated sludge environment include, but are not limited to, Proteobacteria, a physiologically diverse group of microorganisms that represents five subdivisons ($\alpha$, $\beta$, $\gamma$, $\epsilon$, $\delta$), (Madigan et al. Biology of Microorganisms, $8^{th}$ ed. Prentice Hall Upper Saddle River, N.J. 1997). Specific examples of bacterial genera that are expected to work or be involved in the activated sludge environment include, but are not limited to, Paracoccus, Rhodococcus, Pseudomonas, Alcaligenes, Acinetobacter, Sphingamonas, Azoarcus, and Burkholderia.

Internal Storage Molecules

The production of an internal storage molecule is used within the methods of the present invention to monitor and control bioreactor health, to predict and assess bioreactor catalytic efficiency, and to maintain an activated sludge environment. This internal storage molecule may be a class of molecules, collectively termed polyhydroxyalkanoates (PHA), or glycogen, or the like. Both PHA and glycogen have been extensively studied as energy-storage compounds (see Dawes and Senior, 1973. *Adv. Microb. Physiol.* 10:135–266) but their regulation is not clearly understood. In a preferred embodiment of the present invention, this internal storage molecule is polyhydroxyalkanoates (PHA).

Polyhydroxyalkanoates

The terms "polyhydroxyalkanoates" or "PHA" are used herein as generic terms for a class of molecules that are primarily linear, head-to-tail polyesters composed of 3-hydroxy fatty acid monomers that accumulate in microbes as carbon and energy storage molecules (see Madison and Huisman, 1999. *Microbiol. Mol. Biol. Rev.*, 63:21–53; and Byrom, 1994. In: Mobley, ed. Plastics from Microbes, Hanser Publishers, New York, pp. 5–33 for reviews). These polymers are generally synthesized in a broad range of bacteria when the cells have adequate carbon supplies but are limited for another nutrient, such as nitrogen, phosphate, or oxygen.

The terms "polyhydroxyalkanoates" or "PHA" refer to a class of compounds of the general formula:

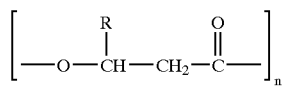

where $R=CH_3$ or $CH_3(CH_2)_m$, where m=1 to 10, and n=4,000 to 20,000 (Mobley, D, editor. Plastics From Microbes. Hanser Publishers, New York, 1994).

The most commonly occurring PHA molecules are polyhydroxybutyrate (PHB) and polyhydroxyvalerate/polyhydroxybutyrate co-polymer that results from a condensation of two molecules of acetyl CoA to form 3-hydroxybutyryl CoA or acetyl CoA with propionyl CoA to form 3-hydroxyvaleryl CoA. These activated molecules are then incorporated into the polymer.

In addition to the 3-hydroxyalkonoates described above, some bacteria have the ability to incorporate longer chained 3-hydroxy acids (carbon length up to $C_{14}$) into the backbone of the polymer (see Byrom, 1994 supra). A list of monomers and functional groups that have been found in microbial PHA is disclosed in Table 2.5 of Byrom (1994). Typically, the composition of the resulting PHA depends upon the growth substrate used (Madison and Huisman, 1999, supra). While the loci encoding PHA synthesis genes have been characterized for at least 18 different species, PHA biosynthesis and its coordinated gene expression in response to environmental conditions remains unclear and represents a complex area under current investigation.

Quantitation of PHA Levels

PHA levels within a sample can be determined or measured for example, by removing an aliquot of the biomass from the reactor and determining its dry weight. Briefly, the biomass is lysed by addition of 0.1 mL of concentrated hydrochloric acid and 0.4 mL of n-propanol, and heat treatment at 100° C. for 2 hours. During this lysis step, polyhydroxyalkonoates are hydrolyzed and esterified. The esterified compounds can then be quantitated by gas chromatography (GC) as described by Riis and Mai, (Riis and Mai (1988) supra) and the dry weight percent PHA calculated.

PHA levels can also be determined using an automated fluorescence based PHA method based upon that described by Ostle and Holt, 1982 (*Applied and Environmental Microbiology*, 44:23) and modified as described below. Briefly, one milliliter of biomass is transferred from the bioreactor to a chamber into which is added 1 mL of Nile Blue (1%). The mixture is incubated at 55° C. for 15 min. The sample is washed with deionized water (or some suitably "clean" non-fluorescent liquid) to remove the excess Nile Blue dye followed by an 8% acetic acid wash. The stained biomass is transferred to a cuvette/flow cell in a fluorescence spectrophotometer with the excitation wavelength set to 362 nm. The amount of PHA present in the biomass is determined by comparison to a standard curve generated using either neat PHA polymer or biomass containing PHA that has been quantitated using the GC-FID (flame ionization detector) method.

High levels of PHA in the biomass indicate that carbon flow in the cell has been directed toward PHA formation and is an indicator of reduced bioreactor health. PHA production and denitrification compete for reduced forms of nicatinamide deoxyribose [NAD(P)H]. Therefore, PHA formation can be viewed as a non-productive side reaction reducing the performance of the system for the desired reaction, i.e. reduction of nitrate.

Specifically, Applicants have determined that when PHA accumulates to high levels in the biomass (about 15 to about 20% dry weight), then utilization of exogenously supplied carbon (methanol and organic acids) slows. Appropriate adjustment of the feed nutrients to the bioreactor can then be made to return the bioreactor to an efficient operating condition. Applicants' observation that high levels of PHA in the biomass correlate to reduced denitrification activity can be used to more rapidly assess the productivity of anoxic wastewater reactors. Since the build up of PHA in bacteria is primarily driven by nutrient limitation (sulfate, sulfide, phosphate, and a nitrogen source, such as nitrate, ammonia, and/or urea), the flux of carbon into PHA can be easily controlled by monitoring key nutrient levels in the effluent.

Wastewater Process Monitoring and Adjustments in Response to Increased PHA Level The overall goal of wastewater systems is to reliably and efficiently treat inlet streams (municipal or industrial) to convert organic carbon to carbon dioxide, and in some cases, organic and inorganic nitrogen to gaseous end products. The general strategy is to use monitoring of nutrient and carbon consumption along with PHA levels in the biomass as a gauge of system productivity to ensure performance of the bioreactor.

An indication that the biocatalytic efficiency of the wastewater treatment process is impaired is seen when the polyhydroxyalkanoates concentration is greater than about 15 to about 20 dry weight percent of the biomass. Appropriate adjustment of the feed nutrients to the bioreactor can then be made to return the bioreactor to an efficient operating condition. Preferably, the feed nutrients are adjusted accordingly in the activated sludge environment when the PHA concentration is from about 10 to about 20 dry weight percent of the biomass. More preferably, the feed nutrients are adjusted accordingly in the activated sludge environment when the PHA concentration is from about 10 to about 15 dry weight percent of the biomass.

Maintaining Viable Cultures in a Bioreactor During Reduced or Absent Carbon Influx The present invention also provides the means to maintain an activated sludge system in the absence of carbon influx. Specifically, applicants have developed a method for maintaining biological activity in the absence of carbon influx to the bioreactor. This method is particularly useful during periods of reduced wastewater production, specifically during scheduled shut downs of the manufacturing process, which normally supplies the carbon feed to the bioreactor. Currently, the only recourse to maintain viable biomass within the reactor is to supply it with purchased carbon sources, such as corn steep liquor, molasses, or another cheap carbon source. By understanding the mechanisms that promote PHA accumulation and providing methods to easily monitor and control the amount of PHA present in the biomass, these polymers can be used as internally supplied carbon sources. The ability of most natural bacteria to break down stored carbon for use as a carbon and energy source during periods of starvation is exploited in this method to maintain biological activity in the wastewater bioreactor without the need to purchase carbon sources.

Prior to a scheduled shut down, nutrient limitations can be used to shift the microbial physiology to PHA synthesis. Applicants have shown in Example 3 below that internal PHA is able to function as a carbon source for the biomass during periods of process waste outages. PHA formation can be stimulated by limiting the amount of nitrogen, phosphorous, and/or sulfur sources that is supplied to the biomass. In a specific embodiment, PHA formation can be stimulated by limiting the amount of nitrogen that is supplied to the biomass. The nitrogen source may include but is not limited to ammonia, nitrate, and/or urea. Preferably, nutrient limitation of the biomass will begin from about 8 weeks before to about 2 weeks before shut down. More preferably, nutrient limitation of the biomass will begin from about 8 weeks before to about 6 weeks before shut down. Even more preferably, nutrient limitation of the biomass will begin at about 8 weeks before shut down. The biologically required amount of nutrients can be determined from the growth yield data, carbon load to the reactor and the amount of each nutrient present in biomass (Wastewater Engineering: Treatment, Disposal, and Reuse. Metcalf and Eddy, Inc. $3^{rd}$ Edition. McGraw-Hill, Inc., New York, 1991).

During the shut down period, the level of PHA in the system should be followed to insure that the biomass does not starve. Preferably, the level of PHA in the system will be at least than about 1% to about 5% of the MLSS. More preferably, the level of PHA in the system will be at least than about 3% to about 5% of the MLSS. Even more preferably, the level of PHA in the system will be at least than about 5% of the MLSS. If the PHA level approaches about 1% to 2% of the MLSS, then purchased carbon sources can be supplied to keep the bioreactor viable until wastewater carbon influx is resumed.

EXAMPLES

The present invention is further defined in the following non-limiting Examples. It should be understood that these Examples, while indicating preferred embodiments of the invention, are given by way of illustration only. From the above discussion and these Examples, one skilled in the art can ascertain the essential characteristics of this invention, and without departing from the spirit and scope thereof, can make various changes and modifications of the invention to adapt it to various uses and conditions.

General Methods

Materials and methods suitable for the maintenance and growth of bacterial cultures are well known in the art. Techniques suitable for use in the following examples may be found as set out in *Manual of Methods for General Bacteriology* (Phillipp Gerhardt, R. G. E. Murray, Ralph N. Costilow, Eugene W. Nester, Willis A. Wood, Noel R. Krieg and G. Briggs Phillips, eds), American Society for Microbiology, Washington, DC. (1994)) or by Thomas D. Brock in *Biotechnology: A Textbook of Industrial Microbiology*, Second Edition, Sinauer Associates, Inc., Sunderland, Mass. (1989).

Methods for analysis and determination of components present in wastewater bioreactors can be found in Eaton et al. (*Standard Methods for the Examination of Water and Wastewater*, $19^{th}$ edition, American Public Health Association, Washington, D.C., 1995).

All reagents, restriction enzymes and materials used for the growth and maintenance of bacterial cells were obtained from Aldrich Chemicals (Milwaukee, Wis.), DIFCO Laboratories (Detroit, Mich.), GIBCO/BRL (Gaithersburg, Md.), or Sigma Chemical Company (St. Louis, Mo.) unless otherwise specified.

The meaning of abbreviations is as follows: "h" means hour(s), "min" means minute(s), "sec" means second(s), "d" means day(s), "mg" means milligram, "g" means gram, "uL" means microliters, "mL" means milliliters, "L" means liters, "uM" means micromolar, "mM" means millimolar, "M" means molar, and "ppm" means parts per million.

Bioreactor Operation:

A modified Eckenfelder reactor was operated in continuous mode. The modifications included a water jacket for temperature control and a head plate. The reactor volume was 280 mL and contained an internal settling zone of 50 mL for a total volume of 330 mL, the temperature was maintained at 35° C. and the pH controlled to 7.50+/−0.15. The pH was maintained by addition of 0.1 M NaOH. The flow rate was set to 0.12 mL/min establishing a hydrolic residence time of 1.9 days. The sludge residence time (sludge age) was 20 days. The sludge age was controlled through daily wasting of biomass from the system. Biomass wasting was performed by mixing the contents of the settling and reaction zones and removing $\frac{1}{20}$th of the reactor volume (20 mL/d). The mass of bacteria present in the reactor was determined daily as follows: three milliliters of biomass was filter through a dried, preweighed 1.2 $\mu$M glass filter (Gelman, Ann Arbor, Mich.), the biomass was dried for 1 hour at 105° C. (dry weight) and combusted at 550° C. for 20 minutes (ashe weight). The oxidation reduction potential (ORP), pH, and temperature were continuously logged to a computer through a data acquisition system (IO Tech multiscan with DuPont Scan 1200 V1.3.0 software).

Media Formulation:

The feed to the reactor was prepared in sterile deionized water. Nitric acid was added to bring the concentration of nitrate to 13.5 g/L. Two compositions of organics were used: 1) methanol and 2) a combination of methanol, valeric acid and butyric acid. The methanol feed contained 9.0 g/L and the mixture contained 4.5 g/L methanol, 1.79 g/l valeric acid and 1.96 g/L butyric acid. The pH was adjusted in both feed compositions to approximately 1.3 by the addition of 2 mL of 50% sodium hydroxide.

Nutrient Addition:

The reactor was batch fed (75 $\mu$L/d) of the following nutrient solutions: Solution 1: comprising $Na_2SO4$, 82.0 g/L; $KH_2PO_4$, 65.6 g/L; $H_3BO_3$, 1.1 g/L; $NaMoO_4$, and 0.5 g/L, $NiCl\ 6H_2O$; Solution 2 comprising $F_3Cl\ 4H_2O$, 13.5 g/L); Solution 3 (MnCl 4H$_2$O, 7.0 g/L; CaCl$_2$ 2H$_2$O, 63.3 g/L; MgCl$_2$ 6H$_2$O, 110.3 g/L; CuCl$_2$ 2H$_2$O, 0.5 g/L; CoCl$_2$ 6H$_2$O, 0.8 g/L). During defined periods, ammonia was also added to the system to a final concentration that ranged from about 99 to about 396 mg/L. The amounts of phosphate, sulfate and ammonia were determined by ion chromatography (see below).

Analytical Techniques

COD Analysis:

The chemical oxygen demand (COD) of the feed and in the bioreactor was measured using Hach COD (Hach Corp., Loveland Colo.) vials following the manufacturer's protocol.

Methanol Analysis:

The concentration of methanol in the reactor was determined by GC/FID as described above (Riis and Mai (1988) supra). Briefly, biomass was removed from the reactor and centrifuged at 13,000 rpm in a microfuge (Heraeus Instruments, USA) at 4° C. The supernatant was filtered through a 0.2 micron filter (Gelman). An HP 6890 GC Hewlet Packard instrument containing a HP-5 capillary column was operated using the following parameters: inlet temperature of 250° C., a helium carrier gas flow rate at 1.5 mL/min, a column temperature initially set at 60° C. and ramped to 250° C. at 25° C./min, an FID temperature of 250° C. and a hydrogen gas flow rate of 40 mL/min, an air flow rate of 450 mL/min, and a helium flow rate of 45 mL/min. An injection volume of 2 uL was used with a 20:1 split at the inlet. Cyclopentanone was used as the internal standard and a linear calibration curve for methanol concentrations ranging from 0 to 1000 mg/l ($r^2$ 0.99) was used to determine reactor methanol concentration.

Anion Analysis:

The concentrations of valeric acid, butyric acid, nitrate, and nitrite were determined by Ion Chromotography using a Dionex IC System. Anions were analyzed using the Dionex ion chromatography isocratic method for anion analysis. Briefly, AS11-HC analytical columns with AS11-HC guard were used with a pump flow rate of 1.5 mL/min. The Detector was conductivity and the eluent was 24 mM NaOH. Sample runtime was 16 minutes using an injection volume of 25 μL. The primary anions analyzed were chloride, nitrite, sulfate, nitrate, and phosphate. External standards were used to generate standard curves. Standard concentrations of 0 mg/L, 1 mg/L, 5 mg/L, 10 mg/L, 20 mg/L, and 50 mg/L with $r^2 > 0.99$ for each component were used to generate the standard curves. Samples were taken from the reactor at different times and centrifuged in 1.5 mL micro-centrifuge tubes for 5 min at 13,000 rpm. The supernatant was diluted 1:5 with deionized water and placed on the autosampler for analysis.

Cation Analysis:

Cations were analyzed using the Dionex ion chromatography isocratic method for cation analysis. Briefly, CS12A analytical columns with CS12G guard were used with a pump flow rate of 1.0 mL/min. The detector was conductivity and the eluent was 22 mN H$_2$SO$_4$. Sample run time was 16 min using an injection volume of 15 μL. The primary cations analyzed were sodium, ammonium, potassium, magnesium, and calcium. External standards were used to generate a standard curve. Standard concentrations of 0 mg/L, 5 mg/L, 10 mg/L and 25 mg/L, with $r^2 > 0.99$ for each component were used to generate the standard curves. Samples were taken from the reactor at different times and centrifuged in 1.5 mL micro centrifuge tubes for 5 min at 13,000 rpm. One mL of the sample's supernatant was the placed into a GC screw top vial containing 10 μL of H$_2$SO$_4$ and either placed in the refrigerator at 4° C. or diluted 1:5 with deionized water and placed on the autosampler for analysis.

Nitrous Oxide Analysis:

The dissolved nitrous oxide concentration was determined by the following method. Briefly, a 1 mL reactor sample was placed into a 2.0 mL crimp cap vial and the sample was acidifed by adding 10 μL of concentrated HCL to stop biological activity. Samples were stored at 4° C. until analyzed. Samples were heated overnight at 80° C. to establish equilibrium between the dissolved and gaseous nitrous oxide. Nitrous oxide levels were determined by GC/ECD (HP instruments) using a Supelco 80/100 Porapak Qss column. The inlet and column temperatures were 30° C. and the total gas flow rate was 30 mL/min (5% methane, 95% Argon). The injection was 100 μL of the vial head space and the GC was operated in splitless mode. Nitrous oxide concentration was determined from an external standard curve made using gas standards. 0, 10, and 100 ppm N$_2$0 (Roberts Gas, Co.).

PHA Concentration Determination:

Biomass was removed from the reactor and transferred to a preweighed 7 mL vial and centifuged at 4000 rpm for 10 min in a Sorval SS34 rotor at 4° C. The supernatant was removed and the biomass pellet is dried at 105° C. overnight. The dry weight of the biomass was determined. The mass of bacteria present in the reactor was determined daily as follows: three milliliters of biomass was filter through a dried, preweighed 1.2 μM glass filter (Gelman), the biomass was dried for 1 hr at 105° C. (dry weight) and combusted at 550° C. for 20 minutes (ashe weight).

The common PHB method is derived from the method developed by Riis and Mai (Riis and Mai (1988) supra).

The method is based on the hydrolysis and transesterification of PHB with propanol and hydrochloric acid to hydroxybutryric acid propyl ester. Benzoic acid is used as the internal standard. Briefly, this method involves adding 1 mL of Dichloroethane (DCE), 200 μL of Benzoic acid stock solution (2.0 g Benzoic acid in 50 mL of 1-propanol), and 1 mL of a Propanol-HCl stock solution (1 volume concentrated hydrochloric acid and 4 volumes 1-propanol) to the vial containing the dry biomass sample. The re-suspended sample is then reacted in a heat block for 2 hours at 100° C. with periodic shaking. The sample is then cooled to room temperature and the reaction is quenched by adding 2 mL of deionized water. Five μL of the organic phase (lower phase) is removed and injected into an HP 6890 GC equipped with a HP-5 5% Phenyl Methyl-Siloxane capillary column. The GC analysis parameters used were a gas flow rate of 1.5 mL/min, injection made with the inlet-split mode, with a split ratio=100:1, an inlet temperature of 180° C. with helium as the carrier gas. The column temperature was initially 100° C. and at the end of the method was 225° C. using a 25° C./min ramp rate. The column was held at 100° C. for 0.5 min, and the total run time was 7.0 min. The detector was a flame ionization detector (FID) operated at 275° C. The gas flow rate was 40 mL/min (Hydrogen) and the air flow rate was 450 mL/min with a Helium make up flow of 50 mL/min.

PHA Calibration Standards Preparation Procedure:

The PHA concentration is determined by comparison to standard containing known amounts of PHBA and PHVA (Sigma Chemical company). A 20 g/L PHB/PHV stock solution was prepared by dissolving 100 mg of PHB/PHV in 5 mL dichloroethane (DCE) and heating at 100° C. The vessel comprising this stock solution should be a calibrated sealed vial. After the PHB/PHV goes into solution, it was cooled to room temperature and DCE was added to restore the original volume. This 20 g/L PHB/PHV stock solution and dilutions prepared from it can be used to detect a range of reactor biomass PHA concentrations from 0 mg/ml to about 16.4 mg/ml. The maximum amount of biomass used was approximately 15 mg, therefore, the amount of PHA in the reactor biomass was within the range of the PHA concentrations provided by the standards.

PHA concentration can also be determined using the automated fluorescence method based upon Ostle and Holt (1982) and modified as described above in the Detailed Description of the Invention.

Determination of Denitrification Potential:

Denitrification potential, the rate of reduction of nitrate to nitrogen per unit of biomass, was determined using biomass from an anoxic bioreactor. The biomass was removed from the reactor and transferred to a centrifuge tube, pelleted and washed with a phosphate buffer solution (pH 7.5, 50 mM), and resuspended in an S12 mineral salts media (10 mM $NH_4SO_4$; 50 mM $KPO_4$, pH 7.0; 2 mM $mgCl_2$; 0.7 mM $CaCl_2$; 0.05 mM $MnCl_2$; 0.001 mM $FeCl_3$; 0.001 mM $ZnCl_3$; 1.72 $\mu M$ $CuSO_4$; 2.53 $\mu M$ $COCl_2$; and 2.42 $\mu M$ $NaMoO_2$) and sparged with argon to remove oxygen. The vials contained between 400 to 500 mg/L of reactor biomass. Various carbon mixes and 20 mg/L nitrate-N (wherein 20 mg/L nitrate-N multiplied by 4.5 g $NO_3$/gN=90 mg/L nitrate) were added into anaerobic vials to initiate the reaction. The carbon sources used consisted of the feed composition (50/50 methanol and organic acids), methanol, organic acids (valeric and butyric) and a no carbon control. The reaction using the feed composition contained 33 mg/L methanol, 12.3 mg/L valeric acid and 13.6 mg/L butyric acid. The methanol reaction contained 66 mg/L methanol and the organic acids reaction contained 24.5 mg/L valeric acid and 27.2 mg/L butyric acid. The rates of nitrate removal and carbon consumption were measured as a function of time using the ion chromatography method described above. The studies were performed at 35° C. and pH 7.5, the operating conditions of the anoxic reactor.

Example 1

Correlation Between PHA and Denitrification in Isolated Cultures

This example describes the impact of feed composition on denitrification rates as determined in a continuous anoxic bioreactor. The first operating condition comprised a feed composition comprising 90% methanol, 5% adipic acid, 2.5% cyclopentanone, and 2.5% hexamethylenediamine, referred to herein as "methanol rich feed". The system was operated in this regime for several sludge ages, i.e., equal to the amount of time needed to replace all of the biomass present in the reactor, so that the operating performance and system characteristics using the methanol rich feed could be determined. Following this period, the system was switched to a feed composition comprising 50% methanol, 25% butyric acid and 25% valeric acid, referred to as "organic acid rich feed" (Arrow 1 on FIGS. 1 and 2). The system was maintained on this feed for several sludge ages and characterized at the macroscopic level using measurements of carbon, nitrate/nitrite, and biomass (MLVSS and MLSS). At various times during this operating period, batch studies were used to measure the denitrification uptake rate (NUR) on various carbon sources. The carbon sources used consisted of the feed composition (50/50 methanol and organic acids), methanol, organic acids (valeric and butyric acids), and a no carbon control.

The macroscopic performance of the methanol rich feed system is shown in FIG. 1 and Table 1.

TABLE 1

Reactor Performance without Ammonia Addition

| Day | Feed $NO_3$ Load mg/day | Reactor $NO_3$ mg/L | Effluent $NO_3$ mg/L |
|---|---|---|---|
| 1 | 2246.0 | 8.0000 | 0.0000 |
| 2 | 2184.0 | 0.0000 | 0.0000 |
| 5 | 2278.0 | 8.0000 | 8.0000 |
| 8 | 2278.0 | ND | ND |
| 12 | 1917.0 | ND | ND |
| 25 | 1874.0 | 0.0000 | 13.000 |
| 32 | 1642.0 | 0.0000 | 0.0000 |
| 39 | 2421.0 | 0.0000 | 0.0000 |
| 43 | 2421.0 | ND | 0.0000 |
| 46 | 2328.0 | 0.0000 | 0.0000 |
| 53 | 2384.0 | 0.0000 | 17.000 |
| 60 | 2233.0 | 0.0000 | 0.0000 |
| 62 | 2213.0 | 183.00 | ND |
| 64 | 2213.0 | 4.0000 | ND |
| 67 | 2182.0 | 0.0000 | 0.0000 |
| 71 | 2223.0 | 0.0000 | ND |
| 74 | ND | 0.0000 | ND |
| 75 | 2286.0 | 491.00 | 8.0000 |
| 76 | ND | 0.0000 | ND |
| 81 | 2178.0 | 0.0000 | 0.0000 |
| 82 | 2050.0 | ND | ND |
| 83 | 2060.0 | 40.000 | 0.0000 |
| 88 | 2203.0 | 0.0000 | 0.0000 |
| 90 | 1851.0 | 104.00 | 0.0000 |
| 91 | 1194.0 | 0.0000 | 0.0000 |
| 92 | 1191.0 | 8.0000 | 8.0000 |
| 93 | 0.0000 | ND | ND |
| 95 | 2401.0 | ND | 0.0000 |
| 96 | ND | 83.000 | ND |
| 97 | 2401.0 | ND | ND |
| 98 | ND | 0.0000 | ND |
| 99 | 2286.0 | 0.0000 | ND |
| 101 | ND | 0.0000 | ND |
| 102 | 2300.0 | 8.0000 | 8.0000 |
| 104 | 2181.0 | 8.0000 | 0.0000 |
| 106 | 2170.0 | 0.0000 | 0.0000 |
| 109 | 2250.0 | 8.0000 | 0.0000 |
| 111 | 2151.0 | 46.000 | 8.0000 |
| 113 | 2276.0 | 29.000 | 0.0000 |
| 116 | 2294.0 | 103.00 | 0.0000 |
| 118 | 2143.0 | 94.000 | 8.0000 |
| 120 | 2149.0 | 60.000 | 0.0000 |
| 123 | 2222.0 | 0.0000 | 0.0000 |
| 125 | 2447.0 | 0.0000 | 0.0000 |
| 127 | 2438.0 | 866.00 | 0.0000 |
| 130 | 1865.0 | 0.0000 | 0.0000 |
| 132 | 1782.0 | 81.000 | 0.0000 |
| 133 | ND | 346.00 | ND |
| 134 | 1747.0 | 500.00 | 0.0000 |
| 137 | 2038.0 | 129.00 | 0.0000 |
| 139 | ND | 1641.0 | ND |
| 140 | 1905.0 | 865.00 | 38.000 |
| 143 | 1848.0 | 81.000 | 0.0000 |
| 146 | ND | 433.00 | ND |
| 147 | ND | ND | ND |
| 148 | 1118.0 | 1224.0 | 0.0000 |
| 151 | 1476.0 | 0.0000 | 0.0000 |
| 153 | 1776.0 | 170.00 | 0.0000 |
| 154 | 21.000 | ND | ND |
| 155 | 16.000 | 14.000 | 0.0000 |
| 158 | 11.000 | 16.000 | 0.0000 |
| 160 | 1065.0 | 19.000 | 12.000 |
| 165 | ND | 180.00 | 0.0000 |
| 166 | 236.00 | 264.00 | 0.0000 |
| 167 | ND | 0.0000 | ND |
| 168 | 102.00 | 74.000 | ND |
| 169 | 114.00 | 37.000 | 0.0000 |
| 172 | 117.00 | 0.0000 | 0.0000 |
| 173 | 155.00 | 144.00 | 0.0000 |
| 174 | 554.00 | 17.000 | ND |
| 175 | 1044.0 | 0.0000 | 0.0000 |

Operation on the methanol rich feed composition resulted in robust performance as characterized by no nitrite or low residual nitrate levels in the effluent. Efficiency of denitrification dropped dramatically following the shift to the organic acid rich feed composition (Arrow 1, FIG. 1). The nitrate load to the system was reduced to zero to simulate shut down two times (Arrows 2 and 3, FIG. 1) and residual carbon and nitrate were flushed from the reactor using a 5 mM phosphate buffer, pH 7.5.

Figure 2:
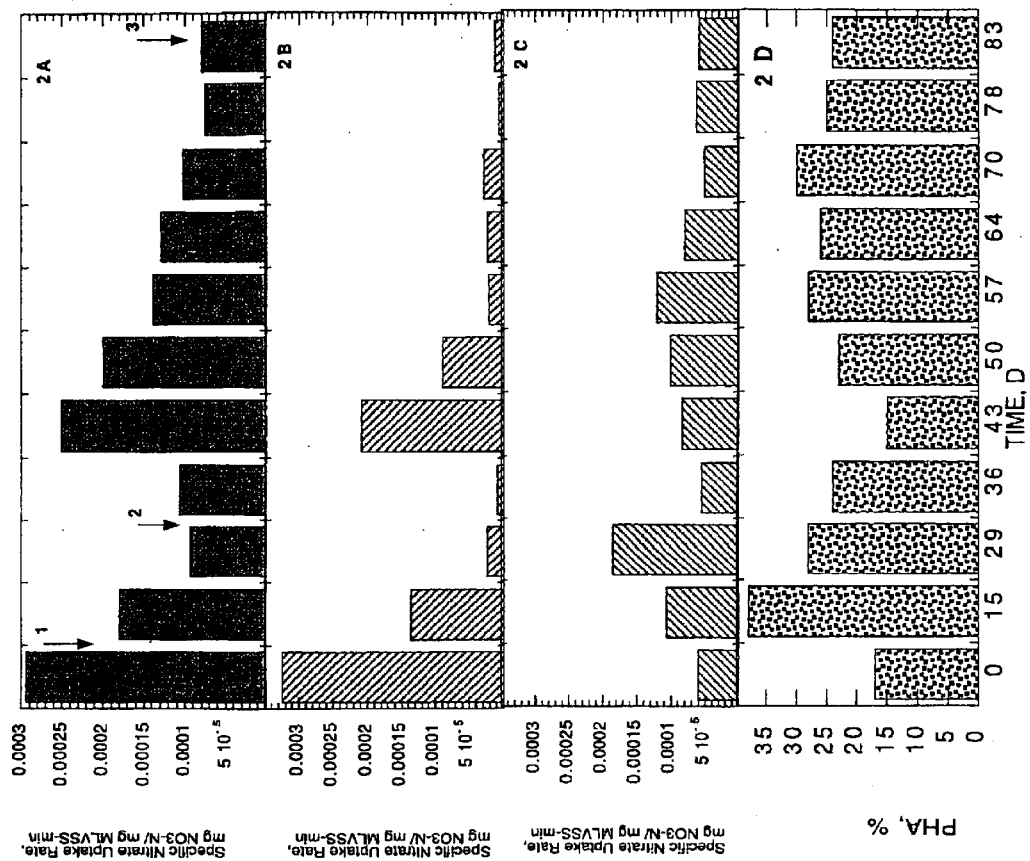
FIG. 2 shows the Reactor Performance over Time in days without Ammonia. 2A: NUR vs. time with organic acid rich feed composition as carbon source. (Arrow 1: Switch from methanol rich feed to organic acids rich feed. Arrow 2: First reactor shut down. Arrow 3: Second reactor shut down.) 2B: NUR vs. time with methanol as carbon source. 2C: No carbon control. 2D: PHA concentration in percent biomass dry weight. NUR=mg nitrate-N/mg MLVSS-min.

The impact of these operating conditions on NUR using various carbon sources and the corresponding reactor PHA levels is shown in FIG. 2. Operation with the methanol rich feed resulted in consistent NUR values in the range $3.35 \times 10^{-4}+/-0.2 \times 10^{-4}$ mg $NO_3$-N/mg MLVSS-min with methanol as the carbon source (FIG. 2A). This denitrification rate is sufficient to ensure complete reduction of the feed nitrate. Following a shift to the organic acid rich feed (Arrow 1 on FIG. 2A), a significant reduction in the rate of denitrification was observed. The NUR with methanol as the carbon source decreased 10 fold within 21 days following the feed shift (FIG. 2B). Also during this period, the endogenous rate increased by 3 fold as determined in the no carbon control shown in FIG. 2C. The increase in the endogenous rate indicates that the biomass was using an internally stored carbon source. However, the NUR with the feed composition was reduced (approximately 3 fold) during in the same time frame (21 days) as shown in FIG. 2A. These data indicate a general reduction in the specific NUR as a function of time following the switch from methanol rich feed to a feed comprising both methanol and organic acids and referred to as the organic acid rich feed. As mentioned above, the reactor was not able to continually metabolize the nitrate and carbon at the rate at which it was being fed. The feed was then switched to a phosphate buffer (pH 7.5) for 24 hours to flush the residual carbon and nitrate from the reactor (Arrow 2 on FIG. 2A). The system was restarted on the organic acid rich feed. The NUR on the organic acid rich feed composition was reduced by approximately 2 fold with the loss of denitrification performance observed within a similar time frame, approximately 21 days (see FIG. 2A) as compared to the first period of operation. The NUR with methanol as the carbon source decreased by a factor of 10 (FIG. 2B). Also consistent with the first period of operation, the endogenous NUR of the second operation increased by a factor of 1.5 (FIG. 2C).

The loss of nitrate reduction performance shown in FIG. 1 (approximately day 95) was reproducible. This behavior was repeated by operating the reactor under the same conditions that resulted in loss of nitrate metabolism. These data are shown in FIG. 1 from 98 to 155 days (between Arrows 2 and 3). The macroscopic characteristics of the system were the same, i.e. reduced nitrate reduction rates and increased levels of PHA in the biomass as shown in FIG. 2. Note the arrow numbers in FIGS. 1 and 2 refer to the same operating periods. These data indicate that the loss of denitrification (nitrate reduction) performance is reproducible and driven by a decreased ability of the biomass to use the exogenously supplied carbon to drive denitrification as indicated by an increased NUR in the no carbon added sample (FIG. 2C). Applicants have herein determined that the internal carbon source present in the biomass is PHA (see FIG. 2D).

Figure 3:
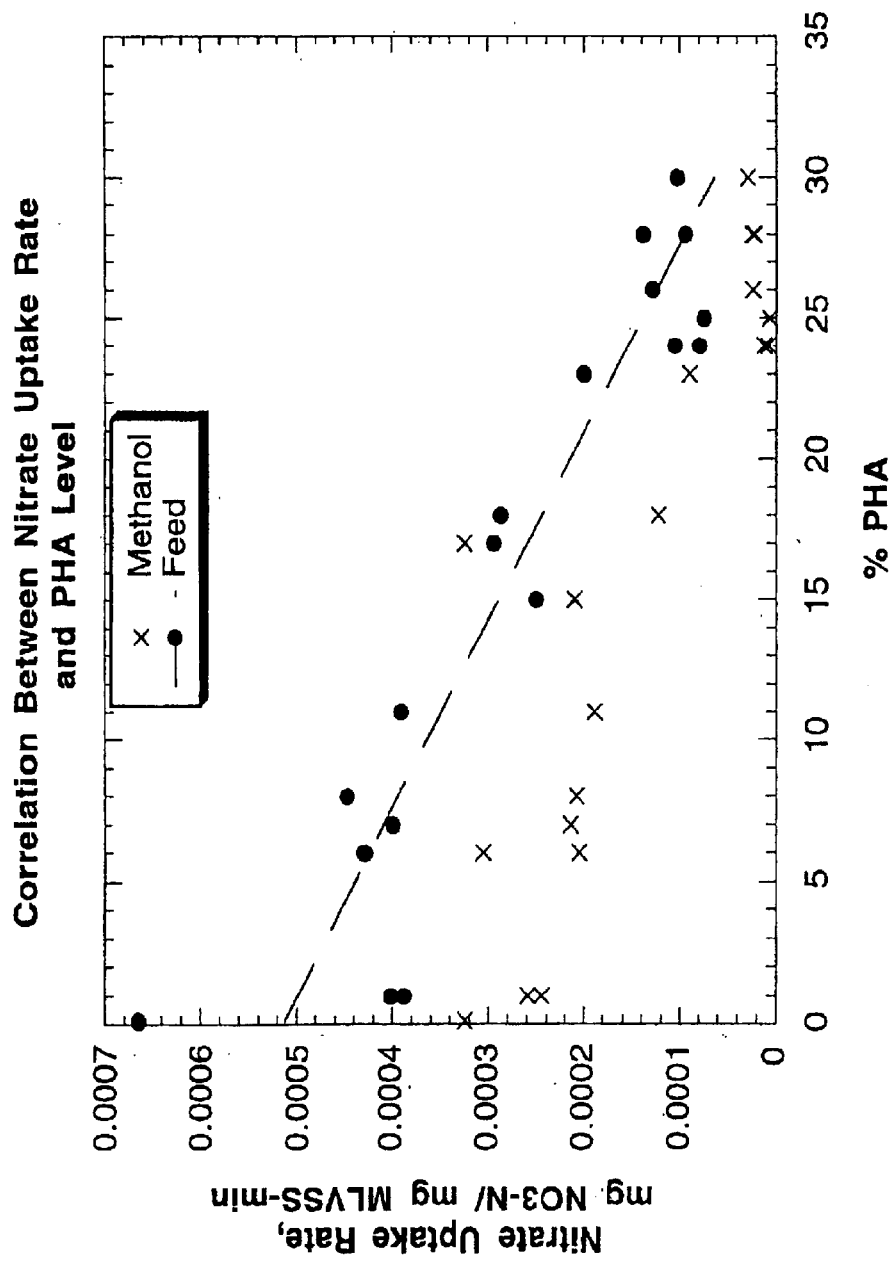
FIG. 3 shows the correlation between Nitrate Uptake Rate (NUR) and PHA Level. NUR with organic acid rich feed composition as carbon source (closed circles). NUR with methanol as carbon source (X). The hatched line represents a linear regression of the organic acid rich feed composition data.

The correlation between NUR and PHA content in the biomass is shown in FIG. 3 and Table 2. The batch NUR measured with the organic acid rich feed composition was reduced by a factor of 3–4 at PHA levels above 15–20%. The data presented in FIG. 3 and Table 2 are a composite of all of the data collected during the various operating conditions.

TABLE 2

Percent maximum specific nitrate uptake rates and percent PHA

| % Maximum SNUR MeOH | % Maximum SNUR Feed | % PHA |
|---|---|---|
| 100.0 | 143.0 | 0.0 |
| 125.0 | 100.0 | 1.0 |
| 75.0 | 84.0 | 1.0 |
| 46.0 | 49.0 | 2.0 |
| 94.0 | 93.0 | 6.0 |
| 63.0 | 92.0 | 6.0 |
| 66.0 | 86.0 | 7.0 |
| 64.0 | 96.0 | 8.0 |
| 58.0 | 84.0 | 11.0 |
| 64.0 | 55.0 | 15.0 |
| 100.0 | 63.0 | 17.0 |
| 80.0 | 86.0 | 18.0 |
| 4.0 | 17.0 | 24.0 |
| 3.0 | 23.0 | 24.0 |
| 2.0 | 16.0 | 25.0 |
| 7.0 | 28.0 | 26.0 |
| 7.0 | 30.0 | 28.0 |
| 7.0 | 20.0 | 28.0 |
| 9.0 | 22.0 | 30.0 |

Although, some of the data fall outside of the general trend, the majority is consistent with the observation that increased PHA levels in the biomass resulted in reduced nitrate uptake rates. With methanol as the carbon source, the NUR was reduced approximately by an order of magnitude at PHA levels above 20%.

The impact of PHA levels on system performance can be determined by comparing the system's nitrate load, which is equal to [feed nitrate (mg $NO_3$-N/L)]×[flow rate (L/min)], to the denitrification capacity in the reactor. The system capacity can be estimated by multiplying the maximum NUR by a PHA inhibition term and the total amount of biomass in the system using Equation 2.

System capacity=[Maximum nitrate rate (mg nitrate-N/mg MLVSS-min)−reduction due to PHA]×[Total biomass in reactor (mg MLVSS)].    EQUATION 2:

The term for the reduction in NUR caused by PHA is determined by linear regression analysis of the data shown in FIG. 3 as shown in Equation 3.

NUR reduction=(1.5×10$^{-5}$ mg nitrate-N/mg MLVSS-min-%PHA)× (%PHA).    EQUATION 3:

The system capacity must be greater than or equal to the nitrate load to the system for complete denitrification to occur. Therefore, Applicants' invention provides one of ordinary skill in the art the ability to monitor PHA levels within the biomass of a wastewater bioreactor and predict the denitrification capacity in the reactor to determine system performance. Appropriate adjustments to the influx, such as nutrient control, can be made similar to that described in Example 2 below to maintain efficient system performance.

Example 2

Effect of the Addition of Various Feed Nutrients on PHA Levels

Example 2 demonstrates that denitrification performance is impacted by PHA level in the biomass. Specifically, an increase in PHA content corresponded to a diminished ability of the biomass to use methanol as a carbon source to drive denitrification (see FIGS. 2 and 3 and Table 2). Accumulation of PHA is a physiological response to excess carbon and nutrient starvation, and can be minimized by the addition of macro- and micronutrients such as ammonia, sulfate, and phosphate. A reactor feed composition was chosen that contained excess ammonia (1.5 times the physiologically required amount) to minimize PHA accumulation and promote reliable denitrification performance.

Figure 4:
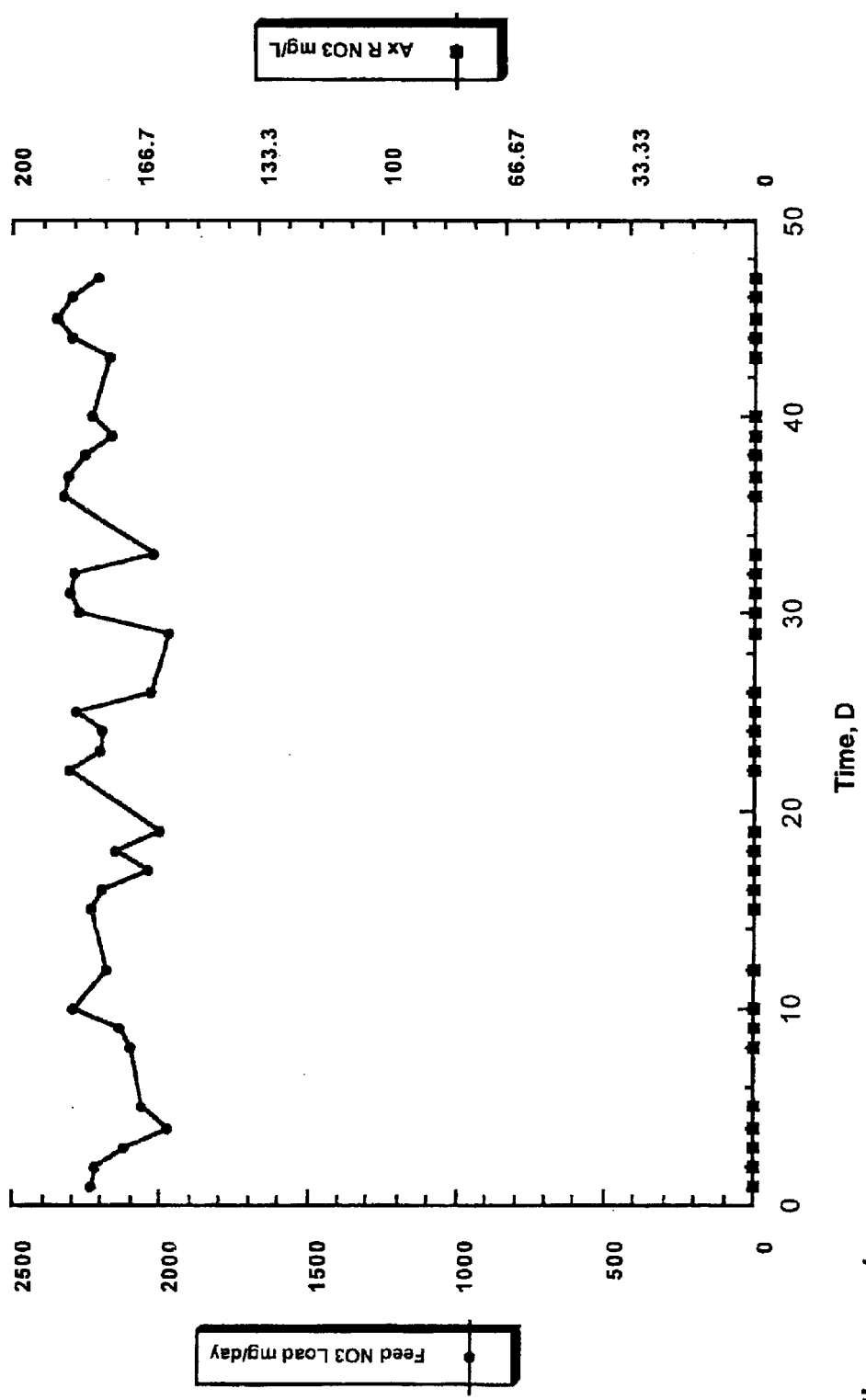
FIG. 4 shows the Macroscopic Reactor Performance with Ammonia Addition. Nitrate load in mg/d (closed circle), Nitrate exiting reactor in mg/L (open square). Lines are drawn to illustrate data trends.

To test the ability of ammonia to control PHA levels in the biomass, the organic acid rich feed composition described in Example 1 was used since PHA levels were higher with this feed composition. The macroscopic performance of the system is shown in FIG. 4. During operation with excess ammonia, the system performance was very stable and reliable and no nitrate leaks were observed. Performance under these reactor conditions contrasts significantly to operation without the addition of ammonia as described in Example 1 (see FIG. 1).

Figure 5:
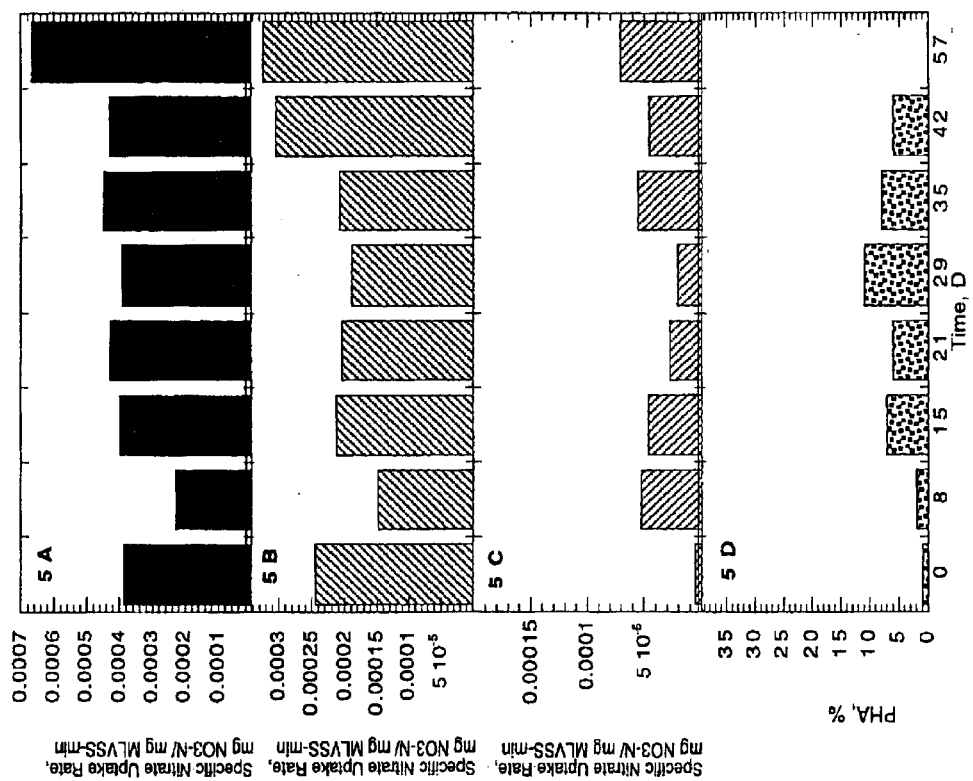
FIG. 5 shows the Reactor Performance over Time with Ammonia Addition. 5A: NUR vs. time with organic acid rich feed composition as carbon source. 5B: NUR vs. time with methanol as carbon source. 5C: No carbon control. 5D: PHA concentration in percent biomass dry weight. NUR= mg nitrate-N/mg MLVSS-min.

NUR experiments were conducted by using biomass from the anoxic bioreactor as described above in Example 1. The nitrate uptake rate using various carbon sources and the corresponding reactor PHA levels are shown in FIG. 5. The NUR with the organic acid rich feed composition as the carbon source with ammonia shown in FIG. 5A resulted in more consistent nitrate removal rates, ranging from $2.82 \times 10^{-4}$ to $6.75 \times 10^{-4}$ mg nitrate-N/mg MLVSS-min. The average feed NUR (organic acid rich feed composition) was approximately 30% higher with ammonia addition than without ammonia addition (compare FIGS. 5A to 2A, respectively). The rate of nitrate removal with methanol as the carbon source ranged from $1.49 \times 10^{-4}$ to $3.24 \times 10^{-4}$ mg nitrate-N/mg MLVSS-min as shown in FIG. 5B. These rates are comparable to the maximum NUR observed during the previous operating regimes (methanol rich feed and organic acid rich feed, both without ammonia addition, FIGS. 1 and 2). The relatively uniform NUR during this period (FIG. 5B) is a sharp contrast to the highly variable NUR rate (methanol as the carbon source) observed during operation with organic acid rich feed without nutrient control (FIG. 2B).

The concentration of PHA in the biomass as a function of operating condition is shown in FIG. 5D. The levels of PHA were approximately two fold higher in the absence of ammonia addition (nutrient control, see FIG. 2D) as compared to operation with nutrient control (FIG. 5D). Without nutrient control, a large fraction (15 to 38%) of the biocatalyst (biomass) is inert polyester (PHA) (FIG. 2D). In contrast, nutrient addition controls the amount of PHA to about 10% or less (FIG. 5D). These results are consistent with the low endogenous NUR observed in the no carbon control reactions as shown in FIG. 5C.

Addition of excess ammonia resulted in reduced levels of PHA in the biomass and consistent nitrate uptake rates. The nitrate utilization rate was approximately 30% higher than the maximum NUR observed in the two previous operating regimes (methanol rich, and organic acid rich, both without ammonia). These results highlight the impact of operating conditions on the performance of an anoxic system and the need to monitor both biomass composition and levels in wastewater bioreactors. Addition of excess ammonia resulted in stable and reliable denitrification performance and reduced levels of PHA in the biomass.

Therefore, monitoring of PHA and nutrient levels in wastewater treatment systems can be used to gauge the denitrification potential and as a general measure of system health. An indication that the biocatalytic efficiency of the wastewater treatment process is impaired is seen when the polyhydroxyalkanoates concentration is greater than about 15 to about 20 dry weight percent of the biomass. Appropriate adjustment of the feed nutrients to the bioreactor can then be made to return the bioreactor to an efficient operating condition. Preferably, the feed nutrients are adjusted accordingly in the activated sludge environment when the PHA concentration is from about 10 to about 20 dry weight percent of the biomass. More preferably, the feed nutrients are adjusted accordingly in the activated sludge environment when the PHA concentration is from about 10 to about 15 dry weight percent of the biomass. Adjustments made to the feed nutrients (i.e., addition of excess ammonia, nitrate, urea, phosphorous sources, sulfur sources, and the like) are effective to achieve optimum health and denitrification ability of the bioreactor.

Example 3

An Activated Sludge System in the Absence Of Carbon Influx

This example describes a method for maintaining biological activity during periods of reduced or absent carbon influx to the bioreactor. This method is useful during periods of scheduled shut downs of the manufacturing process, which normally supplies the carbon feed to the bioreactor, or any other time of significantly reduced carbon influx. Currently, the only recourse to maintain viable bioreactor cultures during a shut-down period is to supply purchased carbon sources such as corn steep liquor, molasses, or another cheap carbon source to the bioreactor. Applicants have identified the conditions under which PHA accumulation can be promoted and provide methods to easily monitor and control the amount of PHA present in the biomass. Since these polymers can be used as internally supplied carbon sources, PHA accumulation can be achieved prior to the scheduled shut down or low carbon influx period. The ability of most natural bacteria to break down the stored PHA for use as a carbon and energy source during periods of starvation can then be exploited in a method to maintain biological activity in the wastewater bioreactor without the need to purchase carbon sources.

Applicants have demonstrated herein that nutrient limitations can be used to shift the microbial physiology to PHA synthesis prior to a scheduled shut down. Specifically, PHA formation can be stimulated by limiting the amount of nitrogen, phosphate, or sulfate that is supplied to the biomass. The biologically required amount of nutrients can be determined from the growth yield data, carbon load to the reactor and the amount of each nutrient present in biomass (Wastewater Engineering: Treatment, Disposal, and Reuse. Metcalf and Eddy, Inc. $3^{rd}$ Edition. McGraw-Hill, Inc., New York, 1991).

Briefly, ammonia addition was gradually withdrawn, starting at about 8 weeks prior to the scheduled shut down. The PHA levels were monitored within the biomass on a 1–2 day basis until PHA levels reached approximately 20% dry weight of the biomass. The carbon influx was stopped and the PHA levels, MLVSS, and nitrate metabolism were monitored using the methods as described above. The amount of PHA in the biomass dropped from 20% to about 2% in one week and a total of 121 mg of nitrate were metabolized (see FIG. 6).

Figure 6:
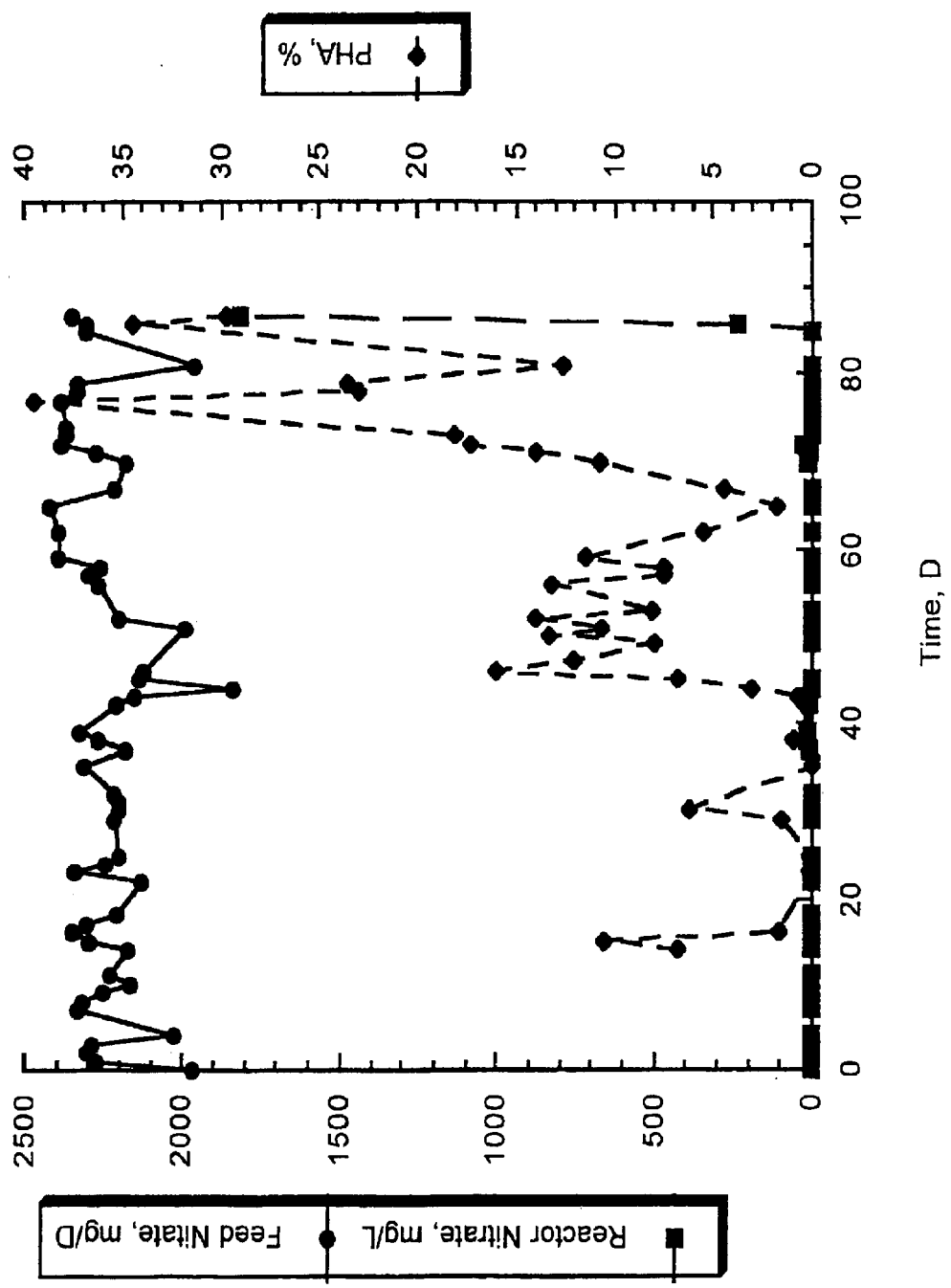
FIG. 6 shows the internal PHA as a carbon source. Closed circles represent PHA weight fraction of the cell mass. Closed squares represent the nitrate concentration in the reactor. Lines are drawn to indicate the trends.
Figure 7:
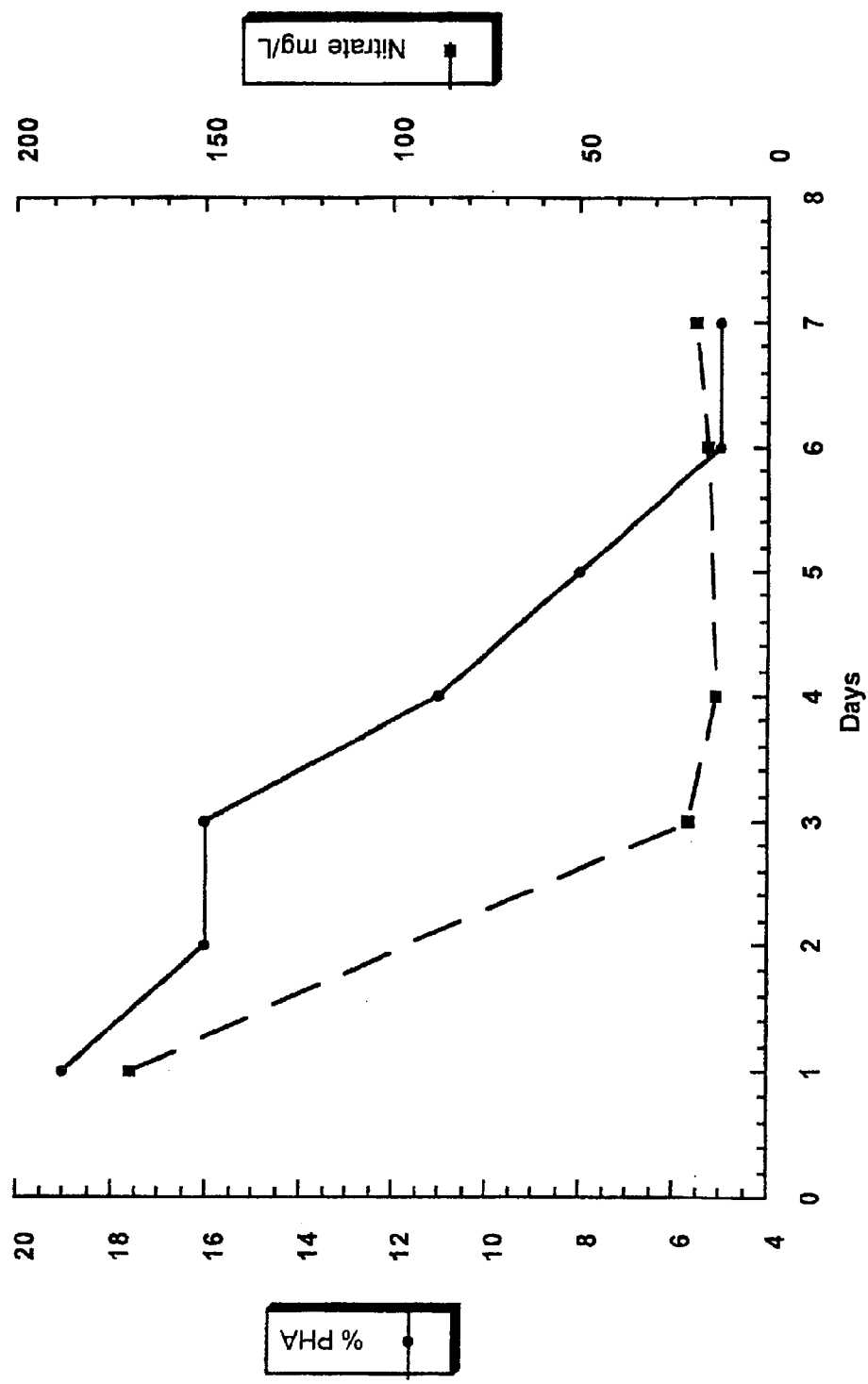
FIG. 7 shows the PHA accumulation during ammonia limitation. Squares represent the nitrate load to the reactor, circles represent the residual nitrate in the reactor and diamonds represent the weight percent of PHA in the biomass.

As shown in FIG. 7, PHA began to build up in the biomass approximately 30 days after ammonia addition ceased. Within approximately 55–60 days (approximately 8 weeks), PHA levels range between 15 and 40 weight percent. As shown in FIG. 6, approximately 20% (PHA wt/biomass wt) PHA was sufficient to support maintenance of the biomass for 6–7 days. Therefore, prior to a scheduled shut down, it is preferable to initiate nutrient limitation about 8 weeks in advance of the shut down to induce PHA accumulation.

These results demonstrate that internal PHA can function as a carbon source during periods of process waste outages, provided that the level of PHA in the system is followed to insure that the biomass does not starve. Preferably, the level of PHA in the system will be at least than about 1% to about 5% of the MLSS. More preferably, the level of PHA in the system will be at least than about 3% to about 5% of the MLSS. Even more preferably, the level of PHA in the system will be at least than about 5% of the MLSS. If the PHA level approaches about 1% to 2% of the MLSS, then purchased carbon sources can be supplied to keep the bioreactor viable until wastewater carbon influx is resumed.

What is claimed is:

1. A method for controlling the biocatalytic efficiency of a wastewater treatment process comprising:
    a) providing an activated sludge environment comprising:
        (i) a carbon influx;
        (ii) cultures of autotrophic, heterotrophic and facultative microorganisms;
        (iii) a feed nutrient; and
        (iv) an end electron acceptor
    b) sampling wastewater from anaerobic, anoxic and/or aerobic stages of the treatment process;
    c) measuring the concentration of an internal storage molecule selected from the group consisting of polyhydroxyalkanoates and glycogen, which is present in the sample, to determine the status of a selected sample characteristic; and
    d) adjusting the feed nutrient in the activated sludge environment depending on the status of the selected sample wherein the biocatalytic efficiency of a wastewater treatment process is controlled.

2. The method according to claim 1, wherein when the concentration of polyhydroxyalkanoates is greater than about 15 to about 20 dry weight percent of the biomass, there is an indication that the biocatalytic efficiency of the wastewater treatment process is impaired.

3. The method according to claim 1, wherein the sampling is in situ.

4. The method according to claim 1, wherein the sampling is continuous.

5. The method according to claim 1, wherein the carbon influx comprises a compound selected from the group consisting of, amines, alcohols, organic acids, carbohydrates, proteins, and amino acids.

6. The method according to claim 1, wherein the cultures of autotrophic, heterotrophic and facultative microorganisms comprise organisms selected from the group consisting of alpha, beta, and gamma Proteobacteria.

7. The method according to claim 6, wherein the alpha, beta, and gamma Proteobacteria are selected from the genera consisting of Paracoccus, Rhodococcus, Pseudomonas, Alcaligenes, Acinetobacter, Sphingamonas, Azoarcus, and Burkholderia.

8. The method according to claim 1, wherein the feed nutrient is selected from the group consisting of nitrate, ammonia, sulfate, sulfide, urea and phosphate.

9. The method according to claim 1, wherein the end electron acceptor is selected from the group consisting of oxygen, nitrate, nitrite, nitrous oxide, ferric oxide, and sulfate.

10. The method according to claim 1, wherein the polyhydroxyalkanoates are comprised of compounds selected from the group consisting of hydroxybutyrate and hydroxyvalerate.

11. The method according to claim 1, wherein the sample characteristic is selected from the group consisting of denitrification efficiency, nitrate concentration, ammonia concentration, sulfate concentration, phosphate concentration, and carbon dioxide concentration.

* * * * *